United States Patent [19]

Furlong et al.

[11] 4,407,153
[45] Oct. 4, 1983

[54] FLUERIC PARTIAL PRESSURE SENSORS

[75] Inventors: Owen D. Furlong, East Coker; Leonard Moore, Somerton, both of England

[73] Assignee: Normalair-Garrett (Holdings) Limited, Yeovil, England

[21] Appl. No.: 243,499

[22] Filed: Mar. 13, 1981

[30] Foreign Application Priority Data

Mar. 17, 1980 [GB] United Kingdom ............... 8008917

[51] Int. Cl.³ .............................................. G01N 7/00
[52] U.S. Cl. .................................. 73/23; 128/204.24; 137/804
[58] Field of Search .......... 73/23; 128/204.24, 204.29, 128/205.11; 137/804, 835, 836, 837

[56] References Cited

U.S. PATENT DOCUMENTS

| 3,490,408 | 1/1970 | Monge et al. | 137/804 |
| 3,665,947 | 5/1972 | Mayer | 137/804 |
| 3,771,348 | 11/1973 | Villarroel | 73/23 |
| 3,817,085 | 6/1974 | Stubbs | 73/23 |
| 4,008,601 | 2/1977 | Woods | 73/23 |
| 4,100,789 | 7/1978 | Joyce | 73/23 |

FOREIGN PATENT DOCUMENTS 2016278 9/1979 United Kingdom .

Primary Examiner—Stephen A. Kreitman
Attorney, Agent, or Firm—Larson and Taylor

[57] ABSTRACT

A flueric partial pressure sensor includes a flueric bridge having two bridge legs adapted for sensing a reference-gas and sample-gas mixture. A linear resistor and an orifice resistor are incorporated in each of the bridge legs which are conjoined to discharge from a single outlet. The resistors are arranged to provide an asymmetric balance of the flow rates through the bridge legs. The asymmetric balance is selected so that in operation a constant pressure output signal is generated for a chosen partial pressure of a constituent gas of the sample-gas mixture in varying absolute pressure conditions such as changes in altitude. Respective pressure signal outlets connected one with each bridge leg at a position between the linear resistor and the orifice resistor are used to effect control of a flueric laminar flow proportional amplifier. Outputs from the flueric amplifier may be used to regulate a fluid mixing valve shown in FIG. 3, or to effect switching of an indicator device shown in FIG. 4.

7 Claims, 4 Drawing Figures

FLUERIC PARTIAL PRESSURE SENSORS

DESCRIPTION OF INVENTION

This invention relates to flueric partial pressure sensors and more particularly to such sensors for sensing the partial pressure of a gas in a gaseous mixture in varying or variable ambient pressure conditions. An area of operation in which such conditions occur is that of aviation where in oxygen control systems for members of aircrew it is required to control the delivery of oxygen to them as a function of altitude so that, irrespective of altitude, oxygen is delivered at an equivalent to a predetermined constant partial pressure.

The term "flueric" as used herein is intended to mean a pure fluidic device that has no moving parts and functions as a result of the effect of its shape channels, volumes and vents on the dynamic properties of the fluid passing therethrough.

BACKGROUND OF INVENTION

Expositions of the prior art are to be found in U.S. Pat. No. 4,008,601 (Woods) and in published U.K. patent application No. 2016278A of the present applicants.

Briefly stated, the Woods U.S. Pat. No. 4,008,601 discloses a flueric partial pressure sensor that enables the partial pressure of a constituent gas of a gaseous mixture to be measured directly relative to a reference-gas by ensuring that the pressure drop output of a flueric bridge concentration sensor is made constant whereby the output pressure signal of the sensor is directly proportional to the partial pressure of the constituent gas at one given absolute pressure.

A sensor according to U.S. Pat. No. 4,008,601 utilises a flueric bridge gas concentration sensor such as is disclosed in U.S. Pat. No. 3,771,348 (Villarroel) having first and second flow channels of equal flueric resistance for receiving a reference-gas and a sample-gas, respectively. Reference and sample-gas flows through the respective first and second flow channels are generated by an aspirator which is essentially operated in its sonic region, or choked flow condition, in order that the reduced pressure created in its aspirated inlet is directly proportional to the ambient pressure. By this means the output pressure of the sensor is directly proportional to the partial pressure of oxygen, or other constituent in the sampled gas mixture.

A disadvantage of a partial pressure sensor arranged in such manner for use in a variable ambient pressure condition is that its pressure signal output for a given partial pressure varies with change in the ambient pressure, i.e. its pressure signal output varies with change in altitude for a given partial pressure of oxygen.

Also briefly stated, the disclosure of U.K. patent application No. 2016278A is directed to apparatus providing breathable gas delivery regulators for working on low supply pressures, below 10 psi (69 kPa), comprising a gas inlet for receiving a breathable gas and a gas outlet for connection to a user between which a demand valve is situated for controlling the flow of gas to the user. A pressure sensor is included which is responsive to the user's breathing pressure and is connected to a control port of a fluidic amplifier of a servo arrangement. The output of the amplifier is connected to an actuator for the demand valve so that the valve is operated in response to breathing pressure signals from the pressure sensor. In a favoured form the regulator includes a breathable gas proportioning valve which allows either of two gases or a mixture thereof to be supplied to the gas inlet and furter includes a flueric gas mixture composition detector means for providing a pressure signal significant of the content of one of the gases in the mixture. This pressure signal is applied as a regulating feedback signal to an actuator of the gas proportioning valve which operates in response to the difference between ambient pressure and absolute pressure.

A component is included in such a regulator for providing absolute pressure to the actuator of the gas proportioning valve and is preferably in the form of an absolute pressure sensor comprising a high recovery venturi with means for inducing a choked flow of ambient air therethrough via a passage of constant cross-section having a tapping for detecting the pressure in the passage to obtain an absolute pressure.

A nuisance value is attributable to the absolute pressure sensor in terms of weight, space and effort required to operate it. All these terms are obviated by use of the present invention which removes the need for such a sensor.

According to one aspect of the present invention a flueric partial pressure sensor including a flueric bridge having two bridge legs adapted for sensing a reference-gas and a sample-gas mixture, respectively, is characterised by being arranged to provide a constant pressure output signal for a predetermined constant partial pressure value of one of the gases in the sample-gas mixture at varying absolute pressure.

In an embodiment of the invention a linear resistor and an orifice resistor are incorporated in each of the two said bridge legs which are conjoined to discharge from a single outlet. Respective pressure signal outlets are connected one with each leg at a position between the linear resistor and the orifice resistor, and the resistors are arranged to provide an asymmetric balance of the flow rates through the two said legs. The asymmetric balance is selected so that, in operation, a constant, or substantially constant, pressure output signal is generated for a chosen partial pressure of a constituent gas of the sample-gas mixture in varying or variable absolute pressure conditions such as changes in altitude.

Extensive experimentation in our laboratories has shown that for a flueric bridge partial pressure sensor having a symmetrical or balanced bridge with air supplied as a reference-gas to one leg and oxygen-enriched air supplied as a sample-gas to the other leg, the pressure output signal changes in direct proportion to the percentage oxygen content of the enriched air providing that the sensor is operated at a fixed absolute pressure or altitude. On the other hand, we have found that with such an asymmetrical bridge circuit bleeding to the control regions of a suitably matched high input impedance flueric laminar flow proportional amplifier the differential output pressure from the amplifier will remain at a constant value over a wide range of absolute pressure conditions (e.g. altitude) when the partial pressure of the sample gas remains constant.

The present invention, in preferred form, introduces a small degree of asymmetry in the flow rates through the reference-gas and sample-gas legs of the bridge sensor and also asymmetry in the relative length/diameter ratios of the orifice resistors which are arranged so that the changing values of their relative coefficients of discharge at various operating pressure ratios causes a degree of differential pressure output that will vary with changes in absolute pressure when identical gas mixtures are passed through the two legs of the bridge.

Accordingly, another aspect of the present invention provides a flueric partial pressure sensor including a flueric bridge having one leg adapted for receiving a reference-gas and another leg adapted for receiving a sample-gas mixture, each said leg including a linear flow resistor and an orifice flow resistor serially arranged therein and being operably connected to flow inducement means for drawing said reference-gas and said sample-gas mixture therethrough, characterised in that said flow resistors are arranged to cause asymmetric flow rates through the respective legs, the orifice resistors providing a small degree of asymmetry in their relative coefficients of discharge so that changing values of coefficients of discharge at various operating pressure ratios causes a degree of differential pressure output from the bridge which varies with changes in absolute pressure when identical gases or gas mixtures are drawn through the bridge legs.

The out of balance, i.e. degree of differential pressure output, can be eliminated when the subject constituent of a gas mixture in the sample leg relative to the other gases therein is re-proportioned so that, despite the overall change in the total pressure of the mixture, the partial pressure of the subject constituent remains constant.

The linear resistors in the legs of the bridge sensor may be positioned either upstream or downstream of the orifice resistors; however, in respect to sensing the partial pressure of oxygen in oxygen-enriched air, it is preferable that the linear resistor is the upstream element of the two, because the reverse arrangement is unnecessarily sensitive and tends to give an unstable device.

The pressure output signal is, in practical usage, amplified and fed as a driving or control signal to pressure responsive means, such as a gas mixing valve or a partial pressure variation indicator device.

As the pressure output signal is in two parts, being derived from the reference-gas leg and the sample-gas leg, it is convenient to use this to operably control the main jet of a flueric amplifier.

BRIEF DESCRIPTION OF THE DRAWINGS

The invention will now be further described by way of example with reference to the accompanying drawings in which.

DETAILED DESCRIPTION OF THE DRAWINGS

Figure 1:
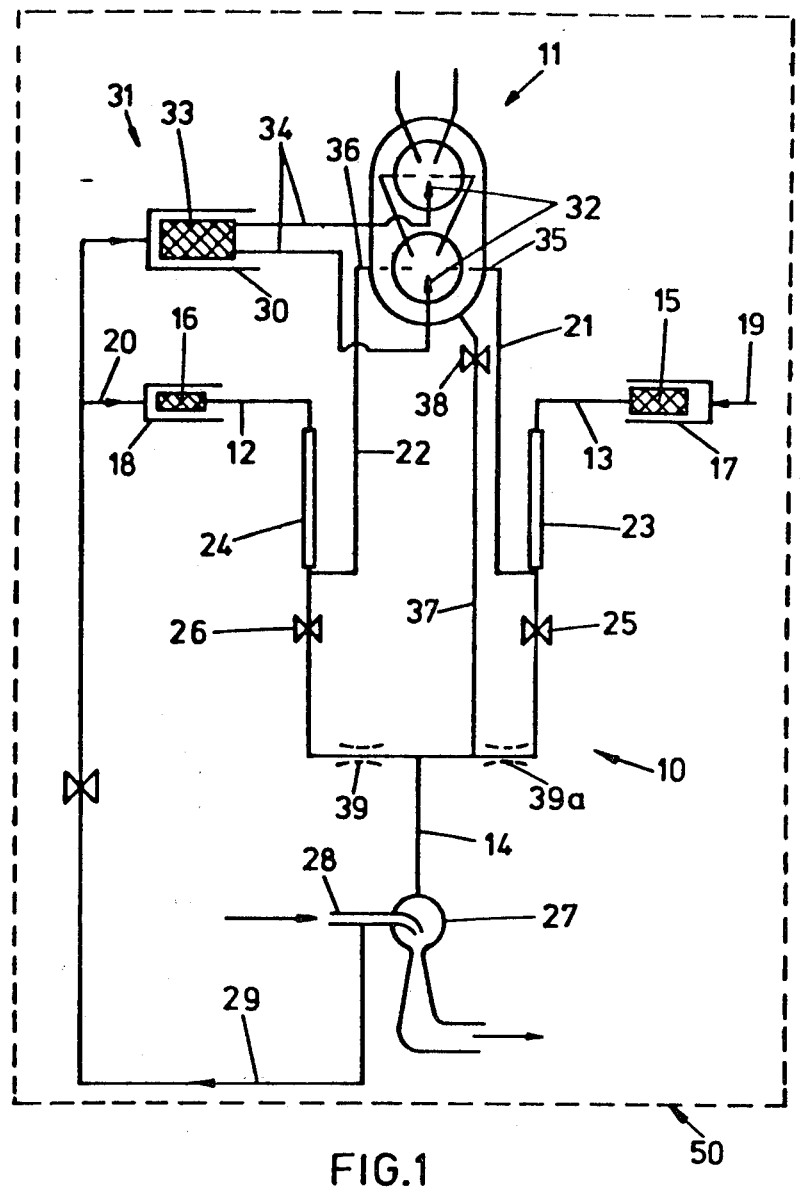
FIG. 1 is a diagrammatic illustration of a flueric partial pressure of oxygen sensor device for use with oxygen-enriched air.

Referring to FIG. 1, a flueric partial pressure of oxygen sensor device 50 comprises a flueric bridge partial pressure sensor 10 and a suitably matched two stage high input impedance flueric laminar flow proportional amplifier 11, the sensor 10 being arranged to provide a constant pressure output signal at varying altitudes for a predetermined constant oxygen partial pressure value. The sensor 10 is designed to operate with a supply pressure of 34.5 kPa and comprises a reference-gas inlet leg 12 for the passage of air and a sample-gas inlet leg 13 for the passage of a gaseous mixture comprising oxygen-enriched air. The two legs conjoin to discharge from a single outlet 14. The sample-gas inlet leg 13 is provided at its entry with a filter 15 that is protected against extraneous contamination by a shroud 17 which connects to a sample-gas supply line 19, whilst a pressure outlet signal passage 21 is connected directly to the leg 13 at a position intermediate a linear resistor 23 and an orifice resistor 25 which is downstream thereof. The reference-gas inlet leg 12 is arranged in a similar manner to that of the sample-gas inlet leg 13 and includes the following corresponding components, a filter 16, a shroud 18 (connected to a reference-gas supply line 20), a pressure outlet signal passage 22, a linear resistor 24 and an orifice resistor 26. The conjoint discharge outlet 14 is connected to a small flueric aspirator 27 that is itself connected to a clean dried air supply line 28 for its operation. A branch conduit 29 is connected to the air supply line 28 for feeding the reference-gas supply line 20 and is further connected to a shroud 30 forming part of an inlet arrangement 31 feeding the main jets 32 of the flueric amplifier 11. In the inlet arrangement 31 a filter 33 is shielded by the shroud 30 and provides entry to separate ducts 34 which are connected to the main jets 32.

Ducts 35, 36 connect the outlet signal passages 21, 22 of the sensor 10, respectively, to the amplifier 11 in its two regions of pressure that effect control of the direction of the first stage main jet 32. A power line 37 for operating the amplifier 11 connects this to the discharge outlet 14 and the aspirator 27. The power line 37 includes an orifice resistor 38, by which means the controlling pressure and sensitivity of the device 50 is predetermined within an available range. A biassing orifice 39 or 39a may be included in one or other of the legs 12, 13 downstream of the orifice resistor therein, as necessary, to obtain a particular predetermined partial pressure or 'set-point'.

The relationship and effect that each of (a) output bias of the amplifier 11; (b) the power line orifice 38; and (c) the biassing orifice 39 or 39a have in respect to the set-point at which the oxygen partial pressure/bridge output value remains constant through a range of altitude is shown for an approximate ground level oxygen partial pressure condition in FIG. 2. The output bias of the amplifier 11 sets the working output pressure of the device, i.e. positions the 'height' of the set-point; the power line orifice 38 in predetermining the sensitivity of the device sets the steepness of the curves; and the biassing orifice 39, 39a modifies the value of the partial pressure required to be significant to the device. Thus by adjustment or selection of the orifices 38, 39, 39a and by matching the amplifier 11 to the sensor 10, an appropriate value of the set-point for a desired partial pressure of oxygen is obtainable.

The linear resistors 23, 24 in the sample-gas inlet leg 13 and the reference-gas inlet leg 12, respectively, are high impedance capillaries operating with a Reynolds Number below 300; whilst the orifice resistors 25, 26, respectively positioned in the legs 13, 12, are of thin disc form. These four resistors are arranged to provide a small asymmetry of flow rates through the two inlet legs 12, 13, giving a difference in flow rates of substantially 10 cc/min. in respect to the capillaries and 6 cc/min. in respect to the orifices with the flow rates through the legs being in a range approximating 200/300 cc/min., with the higher flow rate through the reference-gas (air) inlet leg 12. Also the orifice resistor 26 in the reference-gas leg 12 is of shorter length (0.216 mm) than that of the orifice resistor 25 (0.254 mm) in the sample-gas leg 13, the orifice diameters (0.172 mm) being the same, such that at various operating pressure ratios the output signal from the bridge remains constant in varying absolute pressure while a predetermined partial pressure of oxygen is present in the sample-gas leg. The bias orifice 38 in the power line 37 for the amplifier main jets 32 is selected to produce a pressure greater than, but within 1.4 kPa of, the pressure at the sensor outputs when the bridge is balanced.

In operation of the device 50 clean dried air is supplied to the aspirator 27 by way of the supply line 28 at approximately 0.2 liters/sec. and 31±3.5 kPa. Branch line 29, being connected to the supply line 28, feeds clean dried air to the reference-gas supply line 20 and to the amplifier inlet arrangement 31 at a rate sufficient to prevent the ingress of ambient air to the respective shrouds 18, 30 while allowing ambient pressure to obtain therein. The sample-gas supply line 19, similarly supplies oxygen-enriched air to the shroud 17.

The aspirator 27 creates a sub-ambient pressure in the main jets 32 of the amplifier 11 and throughout the sensor 10 whereby reference-gas (air) is drawn through inlet leg 12 and sample-gas (oxygen-enriched air) is drawn through inlet leg 13 before discharging as a combined flow through outlet 14 and the aspirator 27.

Typical pressures and flows obtaining in the sensor 10 at sea level ambient pressure when the two legs 12, 13 are in a state of balanced pressure, i.e. a predetermined partial pressure of oxygen is being maintained, are as follows:

|  | Pressure downstream of capillary kPa | Pressure downstream of orifice kPa | Flow through linear resistor cc/min | Flow through orifice resistor cc/min |
| --- | --- | --- | --- | --- |
| Reference-gas inlet leg | − 10.4 | − 25 | 270 | 231 |
| Sample-gas inlet leg | − 10.4 | − 25 | 260 | 225 |

While the predetermined partial pressure, i.e. at set-point cross-over (FIG. 2), is maintained the pressure in both outlet signal passages 21, 22 is arranged to be the same and will be effective in the two regions of pressure for controlling direction of the main jet 32 of the first stage of the amplifier 11. However, when the partial pressure of oxygen varies from the predetermined value the flow characteristics in the reference-gas leg and the sample-gas leg 12, 13, respectively, alter and create a pressure difference in the two pressure outlet signal passages 22, 21, so that the pressure regions in the first stage of the amplifier 11 change their pressure at the outlet connections for modifying the response of a pressure responsive device (not shown).

Figure 2:
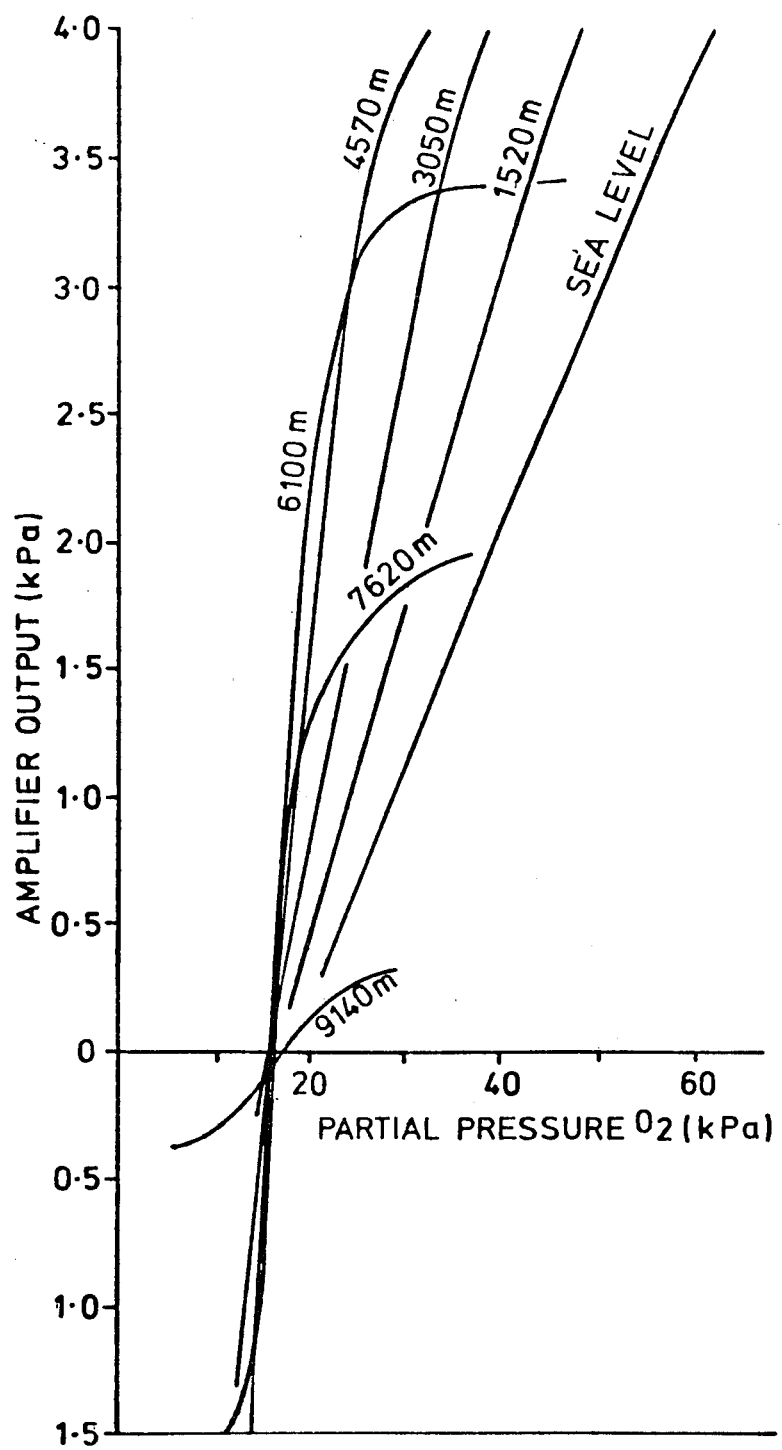
FIG. 2 illustrates, graphically, a common 'set-point' for the sensor device shown in FIG. 1.

Further reference to FIG. 2 shows that a constant oxygen partial pressure/output value common to all output signals given by the device 50 is obtainable through a useful range of altitude from sea level to approximately 9,000 m., which upper limit is imposed by the deterioration in efficiency of the aspirator 27 as the effectiveness of its operating pressure diminishes with increasing altitude. This limitation is not considered to be an embarrassment as in the aviation field the sensor device operates within an aircraft cabin or equivalent pressure region which is normally held at a predetermined pressure that is well below 9,000 m. altitude equivalent. In the event of cabin pressure failure when the equivalent altitude increases the aircrew members are automatically fed a gas mixture appropriate to the situation. Various set-points may be predetermined to satisfy a particular requirement, such as maintaining a supply of oxygen-enriched air at, say, a partial pressure of oxygen equivalent for an altitude of 1,500 m. (i.e. approximately 17.73 kPa), or operating a warning system when the partial pressure of oxygen falls below that required for the chosen set-point.

Figure 3:
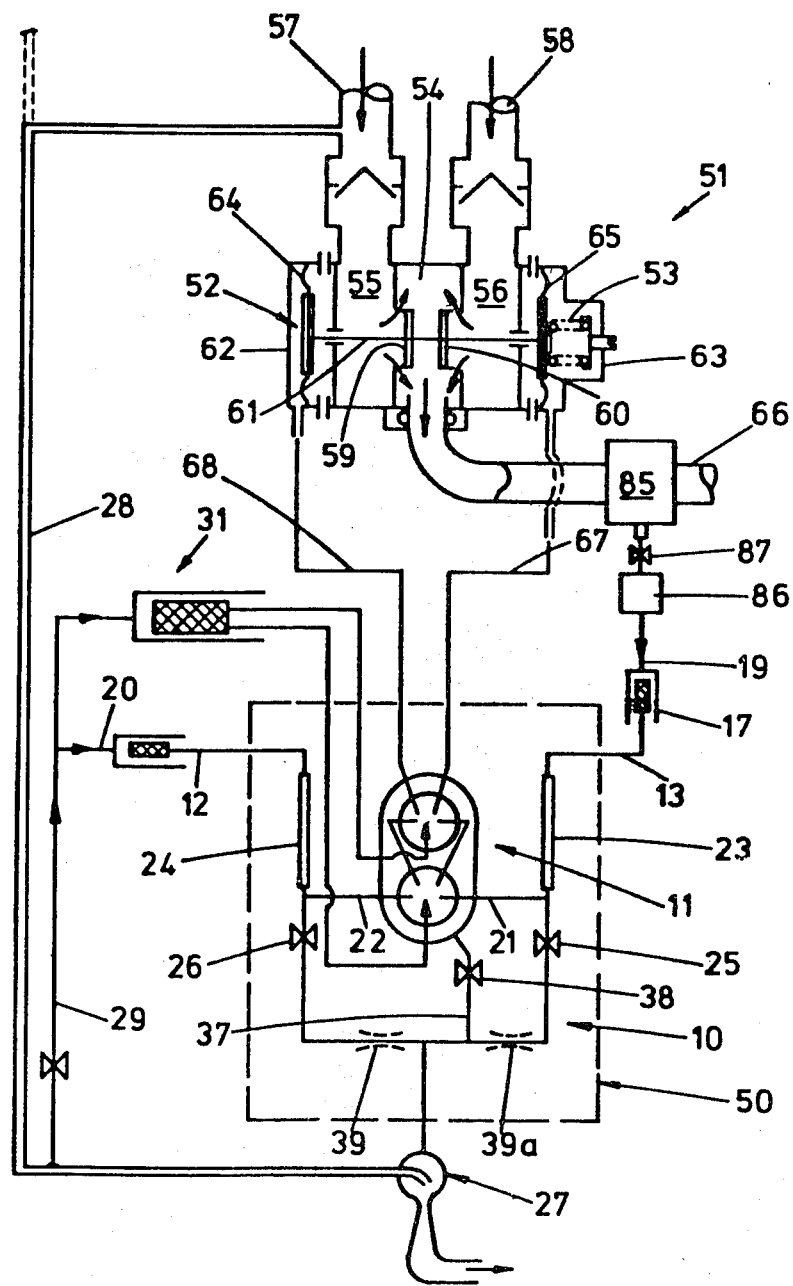
FIG. 3 illustrates diagrammatically a mixing valve for an aviator's breathable gas delivery system in combination with a sensor device as shown in FIG. 1.

In FIG. 3 a flueric partial pressure of oxygen sensor device 50 comprising a flueric bridge partial pressure sensor 10 matched with a two-stage high input impedance flueric laminar flow proportional amplifier 11, as described above with reference to FIG. 1, is used to control a mixing valve 51; the combination providing apparatus for regulation of the composition of oxygen and air for supply to a regulator of an aviator's breathable gas system (not shown). Such a combination provides an improvement over the sensor device and mixing valve shown in FIG. 2 of U.K. patent application No. 2016278A by omitting the absolute-pressure reference device, its operating gas flow and associated ducting, etc., of the arrangement of the application. The mixing valve 51 is similar to, but simpler than, that disclosed in U.K. patent application No. 2016278A and includes a proportioning valve 52 operable in response to pressure signals generated by the sensor device 50.

The mixing valve 51 comprises a mixing chamber 54 positioned between two inlet chambers 55, 56 which admit air and oxygen from respective inlets 57, 58. Admission to the mixing chamber 54 from the chambers 55, 56 is by way of two ports that have circumscribing annular valve seats exposed to the interior of the mixing chamber 54. The proportioning valve 52 includes two valve heads 59, 60 arranged for co-operation with the annular valve seats, being disposed interiorly of the mixing chamber 54 on a common spindle 61 that terminates at each end in a pneumatic actuator arrangement 62, 63. A low rate compression spring 53 is included in one actuator 63 in order to bias the valve heads 59, 60 towards closing the air inlet while opening the oxygen inlet in order to provide a 'fail-safe' condition. The actuator arrangements 62, 63 include diaphragm assemblies 64, 65, respectively, of which the facing sides are connected to ambient pressure whilst their respective remote sides are connected to the pressure output signal passages 67, 68 from the amplifier 11 of the sensor device 50. The air supply line 28 for supplying air to operate the aspirator 27 of the sensor device 50 is connected as a tapping to the air inlet 57. Branch conduit 29 is connected to the air supply line 28 for supplying clean dried air to the inlet arrangement 31 of the amplifier 11 and to the reference-gas supply line 20. The sample-gas supply line 19, for feeding to the sensor device 50, is connected at one end to the delivery line 66 of the mixing valve 51 which conveys air or oxygen or a mixture thereof towards the regulator of the aviator's breathing system (not shown). This connection is made in the vicinity of the regulator and terminates interiorily of a 23 cc capacity 85 which forms part of the delivery line 66. The other end of the supply line 19 terminates at the shroud 17, which shields the filtering end of the sample-gas line 13 of the sensor device 50, and includes a capacity 86 of 14.75 cc which is situated downstream of a flow restrictor 87 that provides an orifice of 0.17 mm diameter. These two capacities 85, 86 and the interposed flow resistor 87 are provided in order to maintain the quality of the sample-gas supplied to the sensor device 50 during a breathing cycle and thereby prevent erroneous output signals emanating from the device. In matching an amplifier 11 with a sensor 10 any inherent bias in its output signal may be conveniently used towards opposing the low rate compression spring 53 in the actuator 63.

In considering operation of the apparatus assume that it is adjusted to maintain a partial pressure of oxygen equivalent to an altitude of 1,500 m. with a balanced condition of the sensor device 50 giving an amplifier output pressure difference of 0.25 kPa (owing to its output bias) and that the aircraft cabin is held at an altitude equivalent above 1,500 m. and below 9,000 m., say, 4,500 m. Conditioned pressurised air, obtained via pressure reducing means from a compressor or compressor stage of an engine of the aircraft (not shown), is supplied to the air inlet 57 and oxygen from, say, an on-board molecular sieve type of oxygen generator is supplied via pressure reducing means to inlet 58, of the mixing valve 51. Air also feeds to the aspirator 27 from the inlet 57 by way of supply line 28 and from this line to the reference-gas supply line 20 and the inlet arrangement 31 of the amplifier by way of branch conduit 29.

The aspirator 27 generates suction to draw reference-gas and sample-gas through the sensor 10 and to effect operation of the main jets of the amplifier 11, as described hereinbefore with reference to FIG. 1. The signal pressures in the outlet signal passages 21, 22 of the sensor 11 are in balance owing to the flow rates appropriate to the partial pressure of oxygen for 1,500 m. obtaining in the inlet legs 12, 13. The low rate spring 53 is arranged to oppose the biased pressure output of the amplifier 11 such that it positions the proportioning valve 52 so as to proportion a flow of oxygen past valve head 60 and air past valve head 59 to obtain oxygen-enriched air having a partial pressure of oxygen corresponding to an 1,500 m. altitude condition.

Should the cabin altitude equivalent subsequently climb the constitution of the air will change, showing a reduction in the oxygen content and consequently 'lean' air will be drawn through the reference-gas inlet leg 12, while enriched air having a correspondingly lower oxygen content will be drawn through the sample-gas inlet leg 13. This will affect the flow rates through the two legs and the output pressure signals in the outlet passages 21, 22 will become unbalanced, with the result that the pressures in the control pressure regions in the first and second stages of the amplifier 11 will vary and the amplifier output change to cause the pressure affecting diaphragm 64 to reduce and that affecting diaphragm 65 to increase so that the proportioning valve 52, assisted by spring 53, moves (to the left in the drawing) and opens further the oxygen valve head 60 while correspondingly closing the air valve head 59.

As the oxygen partial pressure rises, the flow rates in the two inlet legs 12, 13 modify until the pressure output signal from the sensor 10 becomes again balanced. Then the oxygen-enriched air, being supplied to the regulator of the aviator's breathable gas supply system (not shown) by way of the mixing chamber outlet 66, is restored to a condition having a partial pressure of oxygen equivalent to the 1,500 m. altitude condition.

Descent of the cabin altitude equivalent tends to cause slight over-enrichment of the air that is being supplied to the aviator and the effect of the changing reference and sample gases in their respective inlet legs 12, 13 operates in reverse to that just described, so that the output from the amplifier 11 causes the proportioning valve 52 to move towards closing the oxygen valve head 60 while correspondingly opening the air valve head 59 until the fluid flow conditions in the two legs of the sensor 10 return to the corresponding 1,500 m. altitude condition and a balanced pressure output is again established and sensed in the control pressure regions of the first stage of the amplifier 11. Below the preselected set-point altitude equivalent (i.e. preselected partial pressure of oxygen) the apparatus tends to supply slightly oxygen-enriched air in proportion to the slope of the amplifier output line and the amplifier differential output pressure required to oppose the fail-safe spring 53.

Figure 4:
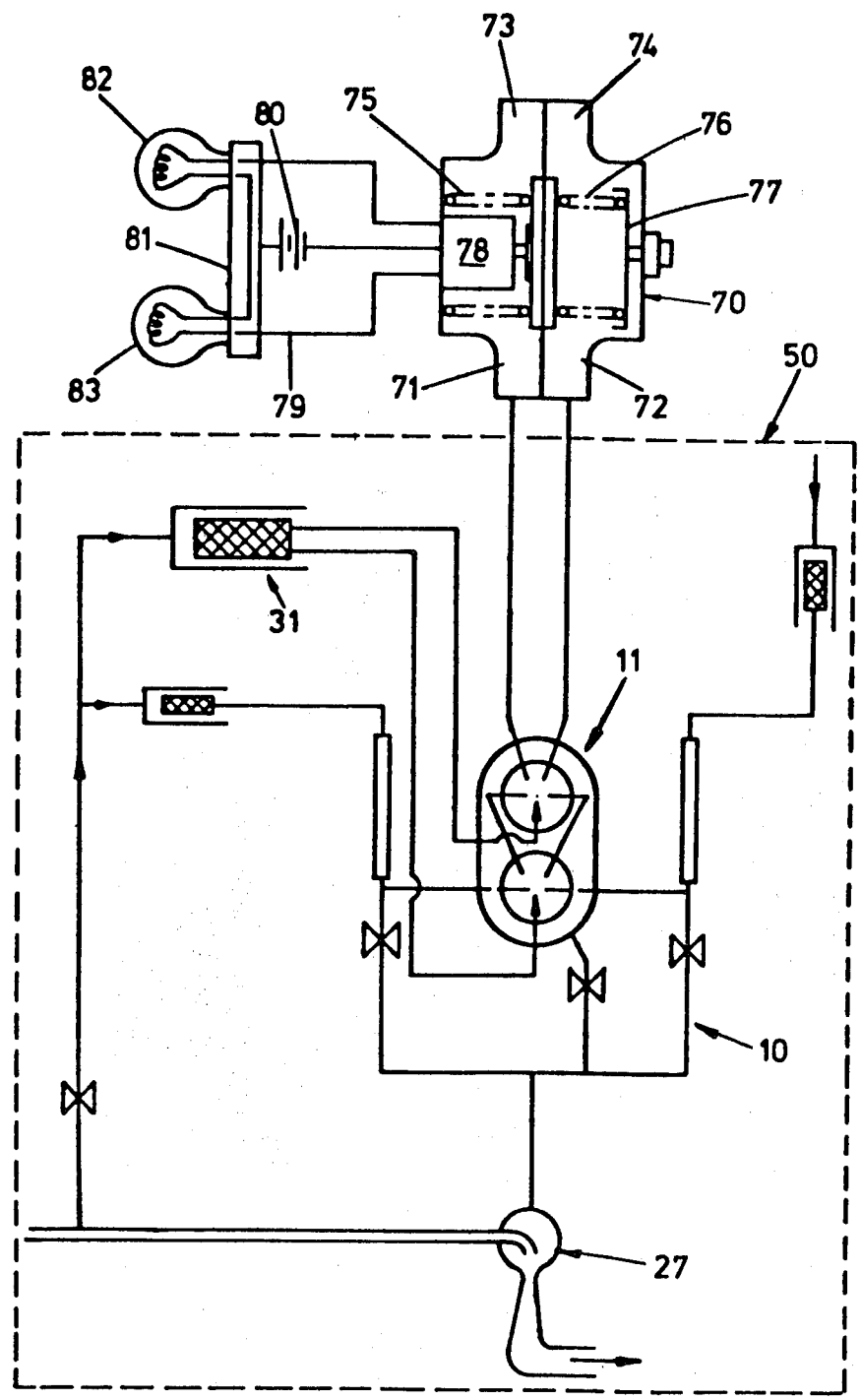
FIG. 4 illustrates diagrammatically a device for indicating the state of a partial pressure of oxygen condition in combination with a sensor device as shown in FIG. 1.

In a further embodiment, as shown in FIG. 4, a flueric partial pressure sensor device 50 is used in combination with a pressure responsive device in the form of an indicator or warning device indicating the state of a partial pressure of oxygen condition. The sensor device 50 is identical to that shown in FIG. 3 and, therefore, will not again be described. The pressure output connections of the amplifier 11 are connected to a pressure transducer 70 which in simple form comprises a housing 71 providing a chamber that is divided by a flexible diaphragm 72 into two sub-chambers 73, 74. The diaphragm 72 is held in a null working position between two opposing low rate compression springs 75, 76, one of which 76 is supported in a screw-type adjuster 77 in sub-chamber 74. A micro-switch 78 is mounted in sub-chamber 73 and arranged to be operated by deflection of the diaphragm 72. The micro-switch forms part of an electrical circuit 79 that includes a power source 80 and an indicator 81 such as an audible or visual device. Provision may be made for visual indication to be continuous by making the micro-switch 78 two-way and providing a form of indicator 81 showing alternative indication, e.g. different coloured lights 82, 83, dependent upon which side of the null position the diaphragm 72 is urged to be by the output signal from the amplifier 11. The pressure output connections of the amplifier 11 are connected to the sub-chambers 74, 73, respectively.

In operation, the sensor device 50 operates as hereinbefore described with reference to the embodiment of FIG. 3. Assuming that the 'set-point', i.e. the partial pressure of oxygen required to be monitored is, say, 17.33 kPa, then, when the oxygen constituent of the sampled gas mixture is at this pressure or greater, the diaphragm 72 is deflected towards sub-chamber 74, owing to the pressure output signals from the sensor 10 being in balance, and the inherent bias of the amplifier 11 causing the micro-switch 78 to complete the circuit 79 to light bulb 82. However, when the partial pressure of oxygen falls below the set-point of 17.33 kPa the sensor 10 pressure output signals are unbalanced and the amplifier output modified so that the diaphragm 72 is deflected towards the other sub-chamber 73 and the micro-switch operated to complete the circuit in activation of light bulb 83.

What is claimed is:

1. A flueric partial pressure sensor including a flueric bridge having two legs, one of said legs sensing a reference gas and the other of said legs sensing a sample gas, means in said legs to provide an asymmetric flow rate through said legs to provide a constant pressure output signal for a predetermined constant partial pressure value of one of the gases in the sample gas mixture at varying absolute pressure.

2. A flueric partial pressure sensor as claimed in claim 1 wherein said means in the two legs includes a linear flow resistor and an orifice flow resistor arranged to provide an asymmetric flow rate through the legs.

3. A flueric partial pressure sensor as claimed in claim 2, wherein the respective orifice flow resistors are of different length/diameter ratio.

4. A flueric partial pressure sensor as claimed in claim 3, wherein the orifice flow resistors comprise two disc orifices of different thickness.

5. A flueric partial pressure sensor as claimed in any one of the preceding claims 1-4 having pressure output signal connections conduitly connected to control regions of a flueric laminar flow proportional amplifier.

6. A flueric partial pressure sensor as claimed in claim 5 in combination with a fluid mixing valve adapted for regulation by pressure chambers connected with outputs from the flueric amplifier.

7. A flueric partial pressure sensor as claimed in claim 5 in combination with an indicator device adapted for switching by outputs from the flueric amplifier.

* * * * *